United States Patent [19]

Hoffmann et al.

[11] Patent Number: 4,728,747
[45] Date of Patent: Mar. 1, 1988

[54] NOVEL 2,3-DISUBSTITUTED BICYCLO(2.2.1)HEPTANES AND HEPTENES, THEIR PREPARATION, AND THEIR USE AS SCENTS

[75] Inventors: Werner Hoffmann, New York, N.Y.; Lothar Janitschke, Kleinniedesheim, Fed. Rep. of Germany

[73] Assignee: Basf Aktiengesellschaft, Ludwigshafen, Fed. Rep. of Germany

[21] Appl. No.: 814,928

[22] Filed: Dec. 30, 1985

[30] Foreign Application Priority Data

Jan. 3, 1985 [DE] Fed. Rep. of Germany ....... 3300057

[51] Int. Cl.$^4$ .......................................... C07C 121/48
[52] U.S. Cl. ................................. 558/428; 560/120; 560/256; 568/374; 568/820; 512/18; 512/14
[58] Field of Search ............... 568/374, 820; 560/120, 560/256; 558/428

[56] References Cited

U.S. PATENT DOCUMENTS

| | | | |
|---|---|---|---|
| 2,877,233 | 3/1959 | Teufel et al. | 558/428 |
| 2,957,906 | 10/1960 | Erickson et al. | 568/374 |
| 3,164,573 | 1/1965 | Schweiker | 560/120 |
| 4,076,853 | 2/1978 | Light et al. | 252/522 R |
| 4,187,243 | 2/1980 | Shaffer et al. | 558/428 |
| 4,228,253 | 9/1980 | Baumann et al. | 558/428 |
| 4,346,243 | 8/1982 | Klemarcyyk et al. | 558/428 |
| 4,549,982 | 10/1985 | Hall et al. | 568/374 |

FOREIGN PATENT DOCUMENTS

| | | | |
|---|---|---|---|
| 0002743 | 7/1979 | European Pat. Off. | 558/428 |
| 2302219 | 9/1977 | Fed. Rep. of Germany | 252/522 R |
| 2333265 | 3/1978 | Fed. Rep. of Germany | 568/374 |
| 2812288 | 4/1983 | Fed. Rep. of Germany | 252/522 R |
| 1279201 | 10/1953 | France | 560/120 |
| 2243174 | 4/1975 | France | 568/820 |

*Primary Examiner*—James H. Reamer

*Attorney, Agent, or Firm*—Oblon, Fisher, Spivak, McClelland & Maier

[57] ABSTRACT

Novel disubstituted bicyclo[2.2.1]heptanes of the general formula I

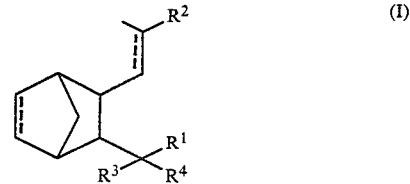

where $R^1$ is $C_1$-$C_3$-alkyl, $R^2$ is $C_1$-$C_8$-alkyl or -alkenyl, $R^3$ and $R^4$ together are =O, =CH—CN, =CH—CO—OCH$_3$ or =CH—CO—OC$_2$H$_5$, or $R^3$ is hydrogen, —CH$_3$, —CH=CH$_2$ or —C≡CH when $R^4$ is —OH or —O—CO—CH$_3$, or $R^3$ is H when $R^4$ is —CH$_2$—CO—OCH$_3$, —CH$_2$—CO—OC$_2$H$_5$ or —CH$_2$—C≡N and one or both of the dashed lines may be a further bond, are obtained by subjecting cyclopentadiene to a Diels-Alder reaction with an unsaturated ketone, this reaction being catalyzed by a Lewis acid, and then subjecting the compound of the formula Ia

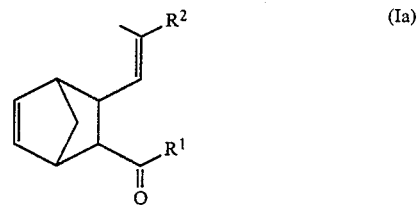

initially formed to a reduction, a Grignard reaction or a reaction with diethylphosphonoacetonitrile or ethyl phosphonoacetate and NaH.

They can be used as scents and/or aromas or as intermediates for scents.

9 Claims, No Drawings

NOVEL 2,3-DISUBSTITUTED BICYCLO(2.2.1)HEPTANES AND HEPTENES, THEIR PREPARATION, AND THEIR USE AS SCENTS

The present invention relates to disubstituted bicyclo[2.2.1]heptanes and -heptenes of the general formula I

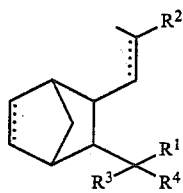

where $R^1$ is $C_1$-$C_3$-alkyl, $R^2$ is $C_1$-$C_8$-alkyl or -alkenyl, preferably methyl, 4-methylpent-3-enyl, 3,4-di methylpent-3-enyl, 4-methylpentyl or 3,4-dimethylpentyl, $R^3$ and $R^4$ together are =O, =CH—CN, =CH—CO—OCH$_3$ or =CH—COOC$_2$H$_5$, or $R^3$ is hydrogen, —CH$_3$, —CH=CH$_2$ or —C≡CH when $R^4$ is —OH or —O—CO—CH$_3$, or $R^3$ is H when $R^4$ is —CH$_2$—CO—OCH$_3$, —CH$_2$—CO—OC$_2$H$_5$ or —CH$_2$—C≡N, and one or both of the dashed lines may be a further bond.

The novel compounds possess surprising and interesting fragrance properties and may therefore become important in the scent industry. Substituted bicyclo[2.2.1]heptanes, some of which possess good organoleptic properties, have been disclosed in German Laid-Open Applications DOS Nos. 2,627,704, 2,623,868, 2,445,395 and 2,624,504 and U.S. Pat. Nos. 4,223,168, 4,187,243 and 3,748,344.

The continuously growing trend toward improving the fragrance of even simple soaps, detergents, and other household products has resulted in a pronounced development of the scent industry. Of particular interest are scents which possess interesting olfactory properties, can be prepared in a very simple manner from raw materials which are easy and cheap to produce industrially, and, because of their chemical structure, are stable and therefore have a very long shelf life. Since the perception of fragrance is an extremely subjective phenomenon, ie. the fragrances of compounds which are found to be extremely pleasant and exciting by one person need not necessarily be perceived in the same way by another person, it is important to have available a very varied range of economical scents which have a long shelf life.

It is an object of the present invention to provide novel scents which possess interesting olfactory properties and can be prepared in a simple manner from starting compounds which are readily obtainable or industrially available in large amounts.

We have found that this object is achieved, and that 2,3-disubstituted bicyclo[2.2.1]heptanes or heptenes are formed in surprisingly good yields when cyclopentadiene, which is available on a large scale industrially, is subjected to a Diels-Alder reaction with an unsaturated ketone, such as 6-methyl-hepta-3,5-dien-2-one or pseudoionone, which is readily obtainable industrially, the Diels-Alder reaction being catalyzed by a Lewis acid, in particular with boron trifluoride etherate. The resulting 2,3-disubstituted bicyclo[2.2.1]heptanes or heptenes themselves possess very good scent properties and can furthermore be converted in a simple and conventional manner to further novel interesting scents.

The present invention therefore also relates to a process for the preparation of disubstituted bicyclo[2.2.1]heptanes of the general formula Ia

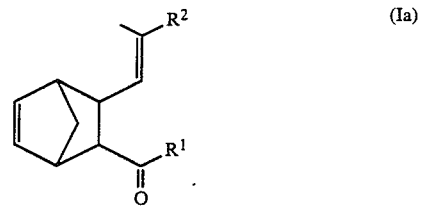

where $R^1$ and $R^2$ have the above meanings, wherein cyclopentadiene (II) is subjected to a Diels-Alder reaction with an unsaturated ketone of the formula III

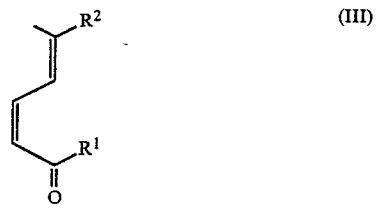

the reaction being catalyzed by a Lewis acid, in particular boron trifluoride etherate. The reaction is carried out in a conventional manner, so that a more detailed description is unnecessary.

In this way, 2-endo-acetyl-3-exo-(2-methylprop-1-en-1-yl)-bicyclo[2.2.1]hept-5-ene was obtained in 87% yield and 2-endo-acetyl-3-exo-(2,6-dimethylhepta-1,5-dien-1-yl)-bicyclo[2.2.1]hept-5-ene in 74% yield.

The unsaturated bicycloheptenes (Ia) can in turn be converted selectively and in good yields to bicycloheptanes or -heptenes of the general formulae Ib and Ic by hydrogenation in a conventional manner.

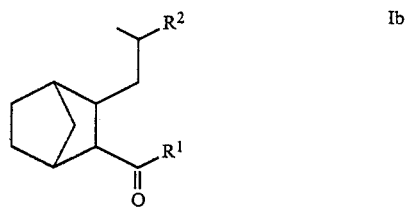

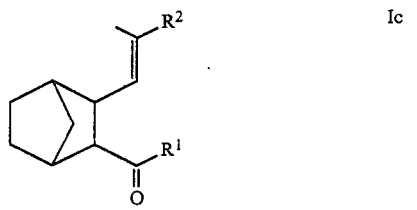

For example, using a catalyst containing 0.5% of Pd on Al$_2$O$_3$, 2-endo-acetyl-3-exo-(2-methylprop-1-en-1-yl)-bicyclo[2.2.1]hept-5-ene was converted to the corresponding saturated compound (Ib) at from 25° to 30° C. and under a hydrogen pressure of 10 bar above atmospheric pressure, and to 2-endo-acetyl-3-exo-(2-methylprop-1-en-1-yl)bicyclo[2.2.1]heptane (Ic) at below 20°

C. and under a hydrogen pressure of 0.3 mbar above atmospheric pressure.

Compounds of the formula Ic can be converted in a conventional manner, by reaction with diethylphosphonoacetonitrile or ethyl phosphonoacetate and NaH in tetrahydrofuran, to the corresponding compounds of the formula I, where $R^3$ and $R^4$ together form =CH—CN (Id) or =CH—COOCH$_3$ or =CH—COOC$_2$H$_5$ (Ie), which in turn can be converted by hydrogenation over a Pd catalyst to the corresponding saturated 2-(1-cyanoprop-2-yl) compounds of the formula If or 2-(1-alkoxycarbonylprop-2-yl) compounds of the formula Ig.

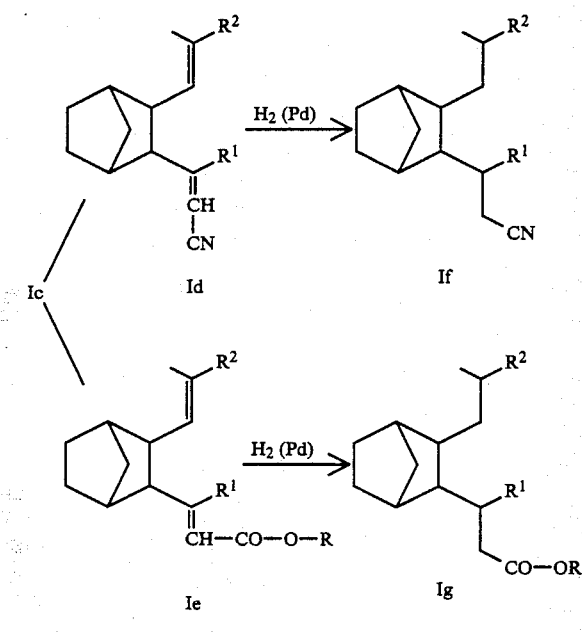

R=—CH$_3$; —C$_2$H$_5$

Compounds of the formula Ih

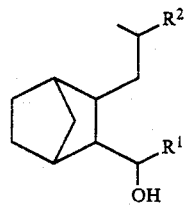

are obtained in high yields by hydrogenating compounds of the formula Ia in the presence of Raney nickel in methanol under elevated hydrogen pressure, or by reacting compounds of the formula Ib with sodium borohydride in ethanol.

Reacting compounds of the formula Ia, Ib or Ic with an organometallic compound in a conventional manner also gives further compounds of the formula Ii having interesting olfactory properties

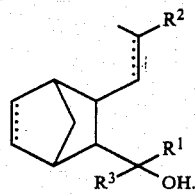

The reactions with methyl-, vinyl- or ethynylmagnesium chloride take place with surprisingly high yields.

In the Examples below, procedures for the preparation of the novel substances are presented, and the fragrances of the compounds prepared are stated.

The compounds of the formula I constitute an enrichment of the range of useful and readily obtainable, fully synthetic scents and aromas. Moreover, they serve as intermediates for the preparation of further scents and aromas.

Particularly interesting scents are 2-endo-acetyl-3-exo-(2-methylprop-1-en-1-yl)-bicyclo[2.2.1]hept-5-ene, 2-endo-acetyl-3-exo(2-methylpropyl)-bicyclo[2.2.1-]heptane, 2-endo-(1-hydroxy-1-methylethyl)-3-exo-(2-methylpropyl)bicyclo[2.2.1]heptane and 2-endo-(2-hydroxybut-3-yn-2-yl)-3-exo-(2-methylprop-1-en-1-yl)-bicyclo[2.2.1]hept-5-ene.

EXAMPLE 1

2-endo-Acetyl-3-exo-(2-methylprop-1-en-1-yl)-bicyclo[2.2.1]hept-5-ene

A mixture of 248 g (2 moles) of 6-methylhepta-3,5-dien-2-one and 150 g (2.27 moles) of cyclopentadiene was added to a stirred solution of 5 ml of boron trifluoride etherate in 500 ml of methylene chloride in the course of 2.5 hours at 25°–30° C. The course of the reaction was monitored by thin layer chromatography, using a 3:1 petroleum ether/ether mixture as the mobile phase. 2 hours after the addition was complete, the mixture was worked up. To do this, about 500 ml of water and 10 g of sodium bicarbonate were added to the reaction mixture, and stirring was continued until the organic phase was found to have a slightly basic pH. Thereafter, the organic phase was separated off, washed with 100 ml portions of water until it was neutral and then evaporated down at 50° C. and 20 mbar. The product which remained was then fractionated very rapidly over a distillation bridge. 279 g (87% yield) of the product and 27 g of unconverted 6-methylhepta-3,5-dien-2-one were obtained.

Bp.=62°–63° C./0.15 mbar; $n_D^{25}$=1.4967
Fragrance: floral, woody, herbaceous.

EXAMPLE 2

2-endo-Acetyl-3-exo-(2,6-dimethylhepta-1,5-dien-1-yl)-bicyclo[2.2.1]hept-5-ene

A mixture of 192 g (1 mole) of 6,10-dimethylundeca-3,5,9-trien-2-one (pseudoionone) and 132 g (2 moles) of cyclopentadiene was added to a stirred solution of 2 ml of boron trifluoride etherate in 500 ml of methylene chloride in the course of 10 minutes under reflux (42°–46° C.). After the reaction had continued for 2 hours, the thin layer chromatogram showed that all the pseudoinone had been converted. The mixture was worked up as described in Example 1, except that the product was distilled continuously in a thin film evaporator at about 80°–110° C./0.5–2 mbar. The oil temperature was 130°–150° C., since it readily cleaves into the starting materials. 191 g (74% yield) of distillate were obtained. Thin layer chromatography showed that this distillate was pure, and the NMR spectrum showed that it had the structure stated above. Distillation of a sample over a 10 ml distillation apparatus gave the following results:

Bp.=110°–112° C./0.06 mbar; $n_D^{25}$=1.5032

Fragrance: slightly camphor-like, woody.

EXAMPLE 3

2-endo-Acetyl-3-exo-(2-methylprop-1-en-1-yl)-bicyclo[2.2.1]heptane 3 g of palladium/alumina (0.5% strength) were added to 95 g (0.5 mole) of 2-endo-acetyl-3-exo-(2-methylprop-1-en-1-yl)-bicyclo[2.2.1]hept-5-ene prepared as described in Example 1, and hydrogenation was carried out at below 20° C. and under a hydrogen pressure of 0.3 bar. When 12 l of hydrogen had been absorbed, the hydrogenation was terminated, the catalyst was filtered off, and the mixture was subjected to fractional distillation to give 75 g of product which, according to the NMR spectrum, was shown to have the structure as stated above.

Bp.=53°–55° C./0.1 mbar; $n_D^{25}$=1.4872

Fragrance: floral, fatty, herbaceous, slightly woody.

EXAMPLE 4

2-endo-Acetyl-3-exo-(2-methylpropyl)-bicyclo[2.2.1]heptane 95 g (0.5 mole) of 2-endo-acetyl-3-exo-(2-methylprop-1-en-1-yl)-bicyclo[2.2.1]-hept-5-ene prepared as described in Example 1 were dissolved in 100 ml of ethyl acetate, 3 g of palladium/alumina (0.5% strength) were added, and hydrogenation was carried out at from 25° to 30° C. and under a hydrogen pressure of 10 bar until absorption of hydrogen was complete. Thereafter, the mixture was filtered, the solvent was distilled off at 50° C. and under 20 mbar, and the produce was isolated by fractional distillation, 87 g (91% yield) being obtained.

Bp.=58°–60° C./0.15 mbar; $n_D^{25}$=1.4650

Fragrance: slightly floral, woody, strongly herbaceous.

EXAMPLE 5

2-endo-Acetyl-3-exo-(2,6-dimethylheptyl)-bicyclo[2.2.1]-heptane 10 g of a palladium/alumina catalyst (0.5% strength) were added to 516 g (2 moles) of 2-endo-acetyl-3-exo-(2,6-dimethylhepta-1,5-dien-1-yl)-bicyclo[2.2.1]-hept-5-ene prepared as described in Example 2, and hydrogenation was carried out at 90° C. and under a hydrogen pressure of 5 bar. When the absorption of hydrogen was complete, the catalyst was filtered off and the filtrate was subjected to fractional distillation. 470 g (89% yield) of a main fraction were obtained.

Bp.=110°–114° C./0.01 mbar; $n_D^{25}$=1.4687

Fragrance: fatty, herbaceous.

EXAMPLE 6

2-(1-Cyanoprop-1-en-2-yl)-3-(2-methylprop-1-en-1-yl)-bicyclo[2.2.1]heptane

A solution of 97.7 g (0.55 mol) of diethylphosphonoacetonitrile in 100 ml of anhydrous tetrahydrofuran was added dropwise to a suspension of 16.5 g of 80% strength sodium hydride (in white oil) in 300 ml of anhydrous tetrahydrofuran at room temperature. The mixture was stirred for 30 minutes, after which a solution of 100 g (0.5 mol) of 97% pure (according to gas chromatography) 2-endo-acetyl-3-exo-(2-methylprop-1-en-1-yl)-bicyclo[2.2.1]heptane in 50 ml of anhydrous tetrahydrofuran was added dropwise to the refluxed mixture. Stirring was continued for 1 hour while heating at the boil, after which the mixture was poured onto 1000 ml of ice water and the organic phase was separated off. The aqueous phase was extracted with 6 times 250 ml of diethyl ether, the ether phases were washed neutral with saturated sodium bicarbonate solution and dried with anhydrous sodium sulphate, and the solvent was distilled off under about 20 mbar and at a bath temperature of not more than 50° C. to give 116.5 g of crude product. Distillation gave 112.7 g of an 85.12% strength product (10.31% of starting material, yield: 80.7% of theory).

Bp.=88°–89° C./0.1 mbar

IR (film) 2 215 cm$^{-1}$, 1 620 cm$^{-1}$ $^{13}$C-NMR (CDCl$_3$/90.52 MHz). 165.21 ppm; 130.81 ppm;

129.87 ppm; 117.33 ppm; 94.65 ppm; 58.40 ppm; 44.56 ppm;

43.84 ppm; 40.41 ppm; 37.66 ppm; 30.06 ppm; 25.74 ppm;

22.72 ppm; 22.02 ppm; 18.33 ppm.

Mass spectrum: 215 m/e, M⊕; 200 m/e M⊕−15

Fragrance: floral, fatty, sourish, amine-like, herbaceous, slightly sweetish.

EXAMPLE 7

2-(1-Ethoxycarbonylprop-1-en-2-yl)-3-(2-methylprop-1-en-1-yl)-bicyclo[2.2.1]heptane A solution of 246 g (1.1 moles) of triethyl phosphonacetate in 200 ml of tetrahydrofuran was added dropwise to a suspension of 33 g (1.1 moles) of 80% strength sodium hydride (in white oil) in 600 ml of anhydrous tetrahydrofuran at room temperature, and the mixture was stirred for a further 30 minutes. 195 g (1 mole) of 2-endo-acetyl-3-exo-(2-methylprop-1-en-1-yl)-bicyclo[2.2.1]heptane were added dropwise to the resulting mixture while heating at the boil, and the mixture was then refluxed for 1 hour. Working up was carried out similarly to Example 6, and 248.2 g of crude product were obtained. Distillation gave 237 g of a product which according to the gas chromatogram was 52.28% strength and contained 38.21% of starting material (yield: 42.9% of theory, or 75.8%, based on converted material). The pure product was obtained by fractional distillation over a 10 cm Vigreux column.

Bp.=85° C./0.1 mbar $^1$H-NMR (CDCl$_3$/60 MHz) 5.63 ppm, very broad, 1H; 4.92 ppm, m, 1H; 4.08 ppm, q (J∼7 Hz), 2H; 2.10 ppm, s, 3H; 1.62 ppm, very broad, 1H; 1.25 ppm, t (J∼7 Hz), 23H;

IR (film): 1 706 cm$^{-1}$, 1 638 cm$^{-1}$.

EXAMPLE 8

2-(1-Cyanoprop-2-yl)-3-(2-methylpropyl)-bicyclo[2.2.1]heptane

A solution of 30.6 g (0.14 mole) of 2-(1-cyanoprop-1-en-2-yl)-3-(2-methylprop-1-en-1-yl)-bicyclo[2.2.1]heptane in 100 ml of ethyl acetate was stirred together with 800 mg of 10% palladium on carbon at 90° C. in a hydrogen atmosphere under 90 bar, until the pressure remained constant for 5 hours.

After the autoclave had been cooled and the pressure let down, the catalyst was filtered off under suction and washed thoroughly with ethyl acetate. The ethyl acetate was distilled off under about 20 mbar to give 24.3 g of crude product. Distillation (bp. ~78° C./0.3) gave 22.8 g of a product which was 87% strength according to the gas chromatogram (yield: 64.6% of theory).

IR: 2 952 cm$^{-1}$, 2 871 cm$^{-1}$, 2 246 cm$^{-1}$, 1 467 cm$^{-1}$, 1,425 cm$^{-1}$, 1 384 cm$^{-1}$, 1 366 cm$^{-1}$, 1 335 cm$^{-1}$, 1 315 cm$^{-1}$, 1 304 cm$^{-1}$, mass spectrum: 219 m/e (M$^{\oplus}$)

Fragrance: slightly sweet, woody, celery-like.

EXAMPLE 9

2-(1-Ethoxycarbonylpropan-2-yl)-3-(2-methyl-1-propyl)-bicyclo[2.2.1]heptane

A solution of 60 g (0.22 mole) of 2-(1-ethoxycarbonylprop-1-en-2-yl)-3-(2-methylprop-1-en-1-yl)-bicyclo[2.2.1]heptane in 100 ml of ethyl acetate was stirred together with 1.6 g of palladium on alumina (0.5% strength) at 90° C. in a hydrogen atmosphere under 150 bar until the pressure remained constant for 5 hours.

Working up was carried out as described in Example 8, and 36.7 of crude product resulted.

Fragrance: cedarwood-like, cinnamic alcohol-like, floral, somewhat terpene-like.

EXAMPLE 10

2-endo-(1-Hydroxyethyl)-3-exo-(2-methyl-1-propyl)-bicyclo[2.2.1]heptane 95 g (0.5 mole) of the 2-endo-acetyl-3-exo-(2-methylprop-1-en-1-yl)-bicyclo[2.2.1]hept-5-ene obtained as described in Example 1 were dissolved in 100 ml of methanol, 3 g of Raney nickel were added and hydrogenation was carried out at 150° C. and under a hydrogen pressure of 50 bar. When the reaction was complete (about 8 hours), the mixture was left to cool, the catalyst was filtered off, and the solvent was distilled off at 20° C. and under 20 mbar. The product which remained was subjected to fractional distillation, 90 g (92% yield) of a main fraction being obtained.

Bp.=74°-75° C./0.1 mbar; $n_D^{245}$=1.4776;

Fragrance: slightly minty, slightly floral.

EXAMPLE 11

2-endo-(1-Hydroxyethyl)-3-exo-(2,6-dimethylheptyl)-bicyclo[2.2.1]heptane 398 g (1 mole) of the 2-endo-acetyl-3-exo-(2,6-dimethylhept-1-yl)-bicyclo[2.2.1]heptane prepared as described in Example 5 were added to a solution of 19 g of sodium borohydride in 1 l of ethanol at below 30° C. in the course of 1 hour. Thereafter, the mixture was left to continue reacting for about a further 16 hours at room temperature, the ethanol was distilled off at 20° C. and under 20 mbar, and the product which remained was hydrolyzed with 2N sulfuric acid until the resulting mixture was slightly acidic. This was extracted with diethyl ether, the ether phase was washed neutral with sodium bicarbonate solution, and the ether was distilled off. In the subsequent fractional distillation of the carbinol, a main fraction of 314 g (86% yield) was obtained.

Bp.=125°-127° C./0.01 mbar; $n_D^{25}$=1.4756.

Fragrance: floral, sweetish, cinnamon-like.

EXAMPLE 12

2-endo-(2-Hydroxybut-2-en-yl)-3-exo-(2-methylprop-1-en-1-yl)-bicyclo[2.2.1]hept-5-ene 380 g (2 moles) of 2-endo-acetyl-3-exo-(2-methylprop-1-en-1-yl)-bicyclo[2.2.1]hept-5-ene were added to 2 l of vinylmagnesium chloride in tetrahydrofuran (2.2 moles) at 25°-30° C. in the course of 1 hour. The mixture was left to continue reacting for about a further hour, after which is was hydrolyzed by adding 220 ml of water, and the precipitated magnesium salt was filtered off. The salt was washed several times with tetrahydrofuran, and the combined tetrahydrofuran solutions were evaporated down at 50° C. and under 20 mbar. The product was then isolated by fractional distillation, the amount obtained being 366 g (84% yield).

Bp.=70°-72° C./0.01 mbar; $n_D^{25}$=1.5043

Fragrance: woody, fatty, lavendar-like.

EXAMPLE 13

2-endo-(2-Hydroxybut-3-yn-2-yl)-3-exo-(2-methylprop-1-en-1-yl)-bicyclo[2.2.1]hept-5-ene 190 g (1 mole) of 2-endo-acetyl-3-exo-(2-methylprop-1-en-1-yl)-bicyclo[2.2.1]hept-5-ene were added to 1 l of ethynylmagnesium chloride in tetrahydrofuran (1.1 moles) at 25°-30° C. in the course of 30 minutes. After the reaction had continued for 1 hour, the mixture was hydrolyzed with 110 ml of water and then worked up by a method similar to that described in Example 5. 166 g (77% yield) of product were obtained.

Bp.=86°-90° C./0.05 mbar; $n_D^{25}$=1.5079

Fragrance: green, herbaceous.

EXAMPLE 14

2-endo-(2-Acetoxybut-3-yn-2-yl)-3-exo-(2-methylprop-1-en-1-yl)-bicyclo[2.2.1]hept-5-ene 62 g (0.6 mole) of acetic anhydride and 0.5 g of phosphoric acid were added to 108 g (0.5 mole) of the compound prepared as described in Example 13, and the reaction mixture was stirred for 24 hours at 25°-30° C., after which it was washed neutral with sodium bicarbonate solution and water, and distilled. 112 g (87% yield) of the acetate were obtained.

Bp.=104°-106° C./0.01 mbar; $n_D^{25}$=1.5016.

EXAMPLE 15

2-endo-(1-Hydroxy-1-methylethyl)-3-exo-(2-methylprop-1-en-1-yl)-bicyclo[2.2.1]heptane 192 g (1 mole) of the 2-endo-acetyl-3-exo-(2-methylprop-1-en-1-yl)-bicyclo[2.2.1]heptane obtained as described in Example 3 were added to 1 l of a 1.5 molar methylmagnesium chloride solution in tetrahydrofuran at below 25° C. in the course of 15 minutes. After about 2 hours, the mixture was hydrolyzed by adding 110 ml of water, the salt formed was filtered off and washed thoroughly with tetrahydrofuran, and the combined tetrahydrofuran solutions were evaporated down at 20° C. and under 20 mbar. The product which remained was then subjected to fractional distillation, 190 g (91% yield) of the carbinol being obtained.

Bp.=62°-63° C./0.3 mbar; $n_D^{25}$=1.4909

Fragrance: woody, herbaceous, sweet note.

EXAMPLE 16

2-endo-(1-Hydroxy-1-methylethyl)-3-exo-(2-methylpropyl)bicyclo[2.2.1]heptane A method similar to that described in Example 15 was used, and the stated cabinol was obtained from the 2-endo-acetyl-3-exo-(2-methylprop-1-en-1-yl)-bicyclo[2.2.1]heptane prepared according to Example 4.

Bp.=63°-64° C./0.4 mbar; $n_D^{25}$=1.4738;

Fragrance: green, slightly minty, camphor-like, woody note.

We claim:

1. A disubstituted bicyclo[2,2,1]heptane or -heptane of the formula:

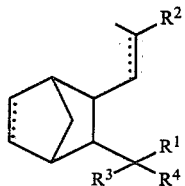

(I)

wherein $R^1$ is $C_1$-$C_3$-alkyl; $R^2$ is $C_1$-$C_8$-alkyl or alkenyl, $R^3$ and $R^4$ together are =CH—CN, =CH—CO—OCH$_3$ or =CH—CO—OC$_2$H$_5$, or $R^3$ is —CH=CH$_2$ or —C≡CH, when $R^4$ is —OH or —O—CO—CH$_3$, or $R^3$ is H when $R^4$ is —CH$_2$—CO—OCH$_3$, —CH$_2$—CO—OC$_2$H$_5$ or —CH$_2$—C≡N and one or both of the dashed lines optionally is a bond.

2. 2-endo-(2-Hydroxybut-3-yn-2-yl)-3-exo-(2-methylprop-1-en-1-yl)-bicyclo[2,2,1]hept-5-ene.

3. 2-(1-Cyanoprop-1-en-2-yl)-3-(2-methylprop-1-en-1-yl)-bicyclo[2,2,1]heptane.

4. 2-(1-Ethoxycarbonylprop-1-en-2-yl)-3-(2-methylprop-1-en-1-yl)-bicyclo[2,2,1]heptane.

5. 2-(1-Cyanoprop-2-yl)-3-(2-methylpropyl)-bicyclo[2,2,1]heptane.

6. 2-(1-Ethoxycarbonylpropan-2-yl)-3-(2-methyl-1-propyl)-bicyclo[2,2,1]heptane.

7. 2-endo-(2-Hydroxybut-3-en-2-yl)-3-exo-(2-methylprop-1-en-1-yl)-bicyclo[2,2,1]hept-5-ene.

8. 2-endo-(2-Hydroxybut-3-yn-2-yl)-3-exo-(2-methylprop-1-en-1-yl)-bicyclo[2,2,1]-hept-5-ene.

9. 2-endo-(2-Acetoxybut-3-yn-2-yl)-3-exo-(2-methylprop-1-en-1-yl)-bicyclo[2,2,1]hept-5-ene.

* * * * *

UNITED STATES PATENT AND TRADEMARK OFFICE
CERTIFICATE OF CORRECTION

PATENT NO. : 4,728,747
DATED : Mar. 1, 1988
INVENTOR(S) : Werner HOFFMANN, et al.

It is certified that error appears in the above-identified patent and that said Letters Patent is hereby corrected as shown below:    Title page:

The Foreign Application Priority Data should read:

-- Jan. 3, 1985   [DE]   Fed. Rep. of Germany ....... 3500057 --

Signed and Sealed this

Twelfth Day of July, 1988

Attest:

DONALD J. QUIGG

*Attesting Officer*    *Commissioner of Patents and Trademarks*